United States Patent [19]
Norton et al.

[11] Patent Number: 6,110,210
[45] Date of Patent: Aug. 29, 2000

[54] PROSTHETIC SPINAL DISC NUCLEUS HAVING SELECTIVELY COUPLED BODIES

[75] Inventors: Britt K. Norton, Eden Prairie, Minn.; Karen R. McRae, Saignon, France; Sinead A. Kavanagh, Galway, Ireland

[73] Assignee: Raymedica, Inc., Bloomington, Minn.

[21] Appl. No.: 09/288,407

[22] Filed: Apr. 8, 1999

[51] Int. Cl.[7] .................................................. A61F 2/44
[52] U.S. Cl. ..................................... 623/17.16; 623/17.11
[58] Field of Search ........................... 623/17.11, 17.16, 623/17.15, 17.12

[56] References Cited

U.S. PATENT DOCUMENTS

| | | |
|---|---|---|
| 3,867,728 | 2/1975 | Stubstad et al. . |
| 3,875,595 | 4/1975 | Froning . |
| 4,349,921 | 9/1982 | Kuntz . |
| 4,772,287 | 9/1988 | Ray et al. ................................. 623/17 |
| 4,904,260 | 2/1990 | Ray et al. ................................. 623/17 |
| 4,911,718 | 3/1990 | Lee et al. ................................. 623/17 |
| 4,932,969 | 6/1990 | Frey et al. ............................... 623/17 |
| 5,047,055 | 9/1991 | Bao et al. ................................. 623/17 |
| 5,123,926 | 6/1992 | Pisharodi ................................. 623/17 |
| 5,171,280 | 12/1992 | Baumgartner ........................... 623/17 |
| 5,192,326 | 3/1993 | Bao et al. ................................. 623/17 |
| 5,401,269 | 3/1995 | Büttner-Janz et al. .................. 623/17 |
| 5,443,514 | 8/1995 | Steffee .................................... 623/17 |
| 5,458,642 | 10/1995 | Beer et al. .............................. 623/17 |
| 5,458,643 | 10/1995 | Oka et al. ............................... 623/18 |
| 5,505,732 | 4/1996 | Michelson ............................... 606/61 |
| 5,507,816 | 4/1996 | Bullivant ................................. 623/17 |
| 5,534,028 | 7/1996 | Bao et al. ................................. 623/17 |
| 5,545,229 | 8/1996 | Parsons et al. .......................... 623/17 |
| 5,549,679 | 8/1996 | Kuslich ................................ 623/17.12 |
| 5,562,736 | 10/1996 | Ray et al. ............................. 623/17.16 |
| 5,571,189 | 11/1996 | Kuslich .................................... 623/17 |
| 5,645,597 | 7/1997 | Krapiva ................................... 623/17 |
| 5,674,295 | 10/1997 | Ray et al. ................................. 623/17 |
| 5,676,701 | 10/1997 | Yuan et al. .............................. 623/17 |
| 5,702,450 | 12/1997 | Bisserie .................................. 623/17 |
| 5,716,415 | 2/1998 | Steffee .................................... 623/17 |
| 5,860,973 | 1/1999 | Michelson ............................... 606/61 |
| 5,865,846 | 2/1999 | Bryan et al. ......................... 623/17.16 |
| 5,893,889 | 4/1999 | Harrington ........................... 623/17.16 |
| 6,001,130 | 12/1999 | Bryan et al. ......................... 623/17.16 |

OTHER PUBLICATIONS

Article entitled, The Artificial Disc Introduction, History and Socioeconoomics, by Charles Dean Ray; pp. 205–225; dated 1992.

Primary Examiner—Paul J. Hirsch
Attorney, Agent, or Firm—Dicke, Billig, Czaja, P.A.

[57] ABSTRACT

A prosthetic spinal disc nucleus comprising a first prosthetic body, a second prosthetic body and a coupling means. The first and second prosthetic bodies each have sufficient structural integrity for maintaining a desired separation between an opposing pair of vertebrae and a volume that is less than a volume of the nucleus cavity. The coupling means selectively associates the first prosthetic body with the second prosthetic body. During use, the first prosthetic body is inserted into a nucleus cavity through an opening in an anulus. The coupling means is configured such that the second prosthetic body does not impede insertion of the first prosthetic body. The second prosthetic body is similarly implanted. Following implant, the coupling means relatively fixes the first and second prosthetic bodies to prevent subsequent movement of the prosthetic spinal disc nucleus, or any portion thereof, back through the opening in the anulus.

27 Claims, 8 Drawing Sheets

PROSTHETIC SPINAL DISC NUCLEUS HAVING SELECTIVELY COUPLED BODIES

BACKGROUND OF THE INVENTION

The present invention relates to a prosthetic spinal disc nucleus. More particularly, it relates to a prosthetic spinal disc nucleus having at least two independent, selectively coupled bodies.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, and a neural (vertebral) arch that arises from a posterior surface of the vertebral body. Each narrow arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The central portions of adjacent vertebrae are each supported by an intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: The nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the opposing vertebral bodies. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into, and released from, the nucleus by cyclic loading. When fluid is forced out of the nucleus, it passes again through the end plates and then back into the richly vascular vertebral bodies. The cyclic loading amounts to daily variations in applied pressure on the vertebral column (e.g., body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the resulting tightening and loosening effect on the anulus stimulates the normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal loading cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

The first prostheses embodied a wide variety of ideas, such as ball bearings, springs, metal spikes and other perceived aids. These prosthetic discs were designed to replace the entire intervertebral disc space and were large and rigid. Beyond the questionable efficacy of those devices was the inherent difficulties encountered during implantation. Due to their size and inflexibility, these first generation devices required an anterior implantation approach as the barriers presented by the lamina and, more importantly, the spinal cord and nerve rootlets during posterior implantation, could not be avoided. Recently, smaller and more flexible prosthetic nucleus devices have been developed. With the reduction in prosthesis size, the ability to work around the spinal cord and nerve rootlets during posterior implantation has become possible.

Generally speaking, these reduced size prostheses are intended to serve as a replacement for the natural nucleus. In other words, the anulus and end plates remain intact, and the prosthesis implanted within the nucleus cavity. It is generally believed that this approach facilitates healing of the anulus. To this end, a number of different prosthetic nucleus designs have been developed. A common concern associated with these designs is minimizing damage or stress on the anulus during implantation. In order to implant a prosthesis within the nucleus cavity, an opening or passage must be created through the anulus. Obviously, the smaller the anulus opening required by the particular prosthetic nucleus design, the lesser the damage caused to the anulus. With this in mind, two general design techniques have been identified for reducing the requisite anulus opening size. First, the prosthesis may be configured to increase from a relatively small size prior to implant, to a larger size following implant. With this approach, the prosthesis will have a reduced size prior to implant, thereby minimizing the requisite opening in the anulus. Alternatively, the prosthesis may include several independent, relatively small portions, each of which are implanted through a correspondingly small opening in the anulus.

For example, Bao et al., U.S. Pat. No. 5,047,055 discloses a prosthetic nucleus made of a hydrogel material that is implanted into the intradiscal space in a dehydrated state. Following implant, the hydrogel material hydrates and expands without constraint to, at least in theory, a shape conforming to the natural nucleus. The device of Bao, as well as other similar products, relies solely upon the natural anulus to constrain expansion of the hydrogel core. This essentially uncontrolled expansion imparts a lateral force directly upon the anulus. In most situations, the anulus is already damaged, and any additional forces placed on the anulus by the prosthesis may impede healing and even cause further deterioration. Further, it is virtually impossible to accurately orientate the dehydrated prosthesis of Bao within the nucleus cavity due to the confined environment presented. Finally, although the disclosure of Bao describes a device having a greatly decreased dehydrated size, it stands to reason that an actual product having a hydrated volume equal to a volume of the nucleus cavity would still have a substantial size in the dehydrated state, regardless of the hydrogel material employed.

An alternative prosthetic nucleus design is described in Ray et al., U.S. Pat. No. 5,674,295. Ray describes a hydrogel-based prosthetic nucleus that is implanted into the intradiscal space in a dehydrated state. The Ray et al. prosthesis includes a jacket sized to constrain expansion of the hydrogel core. More particularly, following implant, the constraining jacket directs the hydrogel core to expand primarily in height, thereby separating adjacent vertebrae. The prosthetic spinal disc nucleus of Ray et al. is sized such that in a final hydrated form, the prosthesis has a volume much less than a volume of the nucleus cavity. In this way, two prostheses can be orientated in a side-by-side fashion within the nucleus cavity. With this dual-prosthesis approach, only a small incision in the anulus is required for implantation. The prostheses are implanted through the small opening, one after the other. Other prostheses, while not being hydrogel-based, similarly follow this dual or multi-component approach.

While the device of Ray, along with other variations, are clearly beneficial, certain concerns may arise. In particular, while the multi-component prosthesis undoubtedly facilitates use of a small anulus opening, because each of the individual components are correspondingly small, there is a possibility that one or more of the components will extrude or eject back through the anulus opening. In other words, each component has a size generally corresponding to a size of the anulus opening. Even if this opening is sewn shut following implant, various forces acting upon the spine may have the potential to "push" one or more of the components back through the anulus opening. Some efforts have been made to address this problem, such as providing the prosthesis component with an expandable tine assembly. Stubstad et al., U.S. Pat. No. 3,867,728 mentions tying two prosthesis segments together with a cord following implant. Unfortunately, due to the highly confined nature of the nucleus cavity, it would be virtually impossible for a surgeon to manipulate the cord extending from one segment around the second segment. In other words, because the cord is not in any way connected to the second segment, the surgeon must establish this connection post-implant. The anulus and opposing end plates render this task highly difficult.

Degenerated, painfully disabling intraspinal discs are a major economic and social problem for patients, their families, employers and the public at large. Any significant means to correct these conditions without further destruction or fusion of the disc may therefore serve an important role. Other means to replace the function of a degenerated disc have major problems such as complex surgical procedures, unproven efficacy, placing unnecessary and possibly destructive forces on an already damaged anulus, etc. Further, unexpected expulsion of the prosthesis, or individual components, from the disc space following implant while uncommon, may be a potential concern. Therefore, a substantial need exists for a prosthetic spinal disc nucleus configured to minimize damage to the anulus and reduce the potential for expulsion following implant.

SUMMARY OF THE INVENTION

One aspect of the present invention provides a prosthetic spinal disc nucleus for implantation within a nucleus cavity defined by opposing vertebrae and an anulus, and a method of manufacturing such a prosthesis. In one preferred embodiment, the prosthesis is comprised of a first prosthetic body, a second prosthetic body and a coupling means for selectively associating the first prosthetic body with the second prosthetic body.

The first prosthetic body can assume a wide variety of shapes and constructions, but preferably has sufficient structural integrity for separating an opposing pair of vertebrae. Further, the first prosthetic body has a volume that is less than a volume of a nucleus cavity. In one preferred embodiment, the first prosthetic body includes a hydrogel core encompassed by a constraining jacket having a generally fixed maximum volume.

The second prosthetic body may also assume a number of different forms and constructions. However, in the preferred embodiment, the second prosthetic body has sufficient structural integrity for separating an opposing pair of vertebrae. Further, the second prosthetic body has a volume that is less than a volume of a nucleus cavity. In one preferred embodiment, the second prosthetic body includes a hydrogel core encompassed by a constraining jacket having a generally fixed maximum volume.

The coupling means selectively associates the first prosthetic body with the second prosthetic body. In this regard, the coupling means is configured to allow successive implantation of the first prosthetic body and then the second prosthetic body through an opening in the anulus. Thus, in one preferred embodiment, the coupling means permits a pre-implant spacing between the prosthetic bodies such that the second prosthetic body does not interfere with implantation of the first prosthetic body. The coupling means is further configured to substantially affix the first prosthetic body to the second prosthetic body upon implantation and final assembly. In this regard, immediately following implantation of the second prosthetic body, the coupling means is connected to both of the prosthetic bodies. With this configuration, the prosthetic spinal disc nucleus can be maneuvered to the final assembly in a relatively rapid fashion. In one preferred embodiment, the coupling means is a biocompatible thread that is slidably secured to, and extends between, each of the first and second prosthetic bodies. With this configuration, in an initial position, an extension of the thread between the first and second prosthetic bodies is variable, whereas in a final position, the extension is relatively fixed.

Another aspect of the present invention relates to a method of manufacturing a prosthetic spinal disc nucleus for implantation into a nucleus cavity. The method includes forming a first prosthetic body having sufficient structural integrity for separating an opposing pair of vertebrae and a volume that is less than a volume of a nucleus cavity. A second prosthetic body is then formed. The second prosthetic body may or may not be similar to the first prosthetic body, but has sufficient structural integrity for separating an opposing pair of vertebrae and a volume that is less than a volume of a nucleus cavity. A coupling device is provided to selectively couple the first prosthetic body to the second prosthetic body such that a distance between the first and second prosthetic bodies is variable in a first state, and relatively fixed in a second state. At least a portion of the coupling device is connected to both of the prosthetic bodies immediately following implantation. In one preferred embodiment, the coupling device is a flexible thread that is slidably connected to at least the second prosthetic body. With this configuration, in the first state, the second prosthetic body can be moved relative to the first prosthetic body by sliding along the flexible thread. Following implantation, the flexible thread can be tied so that the first prosthetic body is relatively fixed to the second prosthetic body.

Another aspect of the present invention relates to a method of implanting a prosthetic spinal disc nucleus into a nucleus cavity. The nucleus cavity is defined by an opposing pair of vertebrae and an anulus. The prosthetic spinal disc nucleus includes a first prosthetic body and a second prosthetic body, each of the prosthetic bodies having sufficient structural integrity to separate the opposing pair of vertebrae and a volume that is less than a volume of the nucleus cavity. The method includes providing a coupling means to selectively couple the first prosthetic body to the second prosthetic body. An opening is then formed in the anulus. The first prosthetic body is inserted into the nucleus cavity through the opening in the anulus. In this regard, the coupling device is configured such that the second prosthetic body does not impede insertion of the first prosthetic body. Further, at least a portion of the coupling device is connected to the first prosthetic body immediately after insertion. Following insertion, the first prosthetic body is lodged in the nucleus cavity. Finally, the second prosthetic body is inserted into the nucleus cavity. At least a portion of the coupling device is connected to the second prosthetic body immediately after insertion. The coupling device is then positioned to closely relate the first prosthetic body with the second prosthetic body so that the first prosthetic body prevents displacement of the second prosthetic body back through the opening in the anulus. For example, in one preferred embodiment, the coupling device is a flexible thread that, following implantation, effectively fixes the first prosthetic body to the second prosthetic body.

DESCRIPTION OF THE PREFERRED EMBODIMENTS

Figure 1:
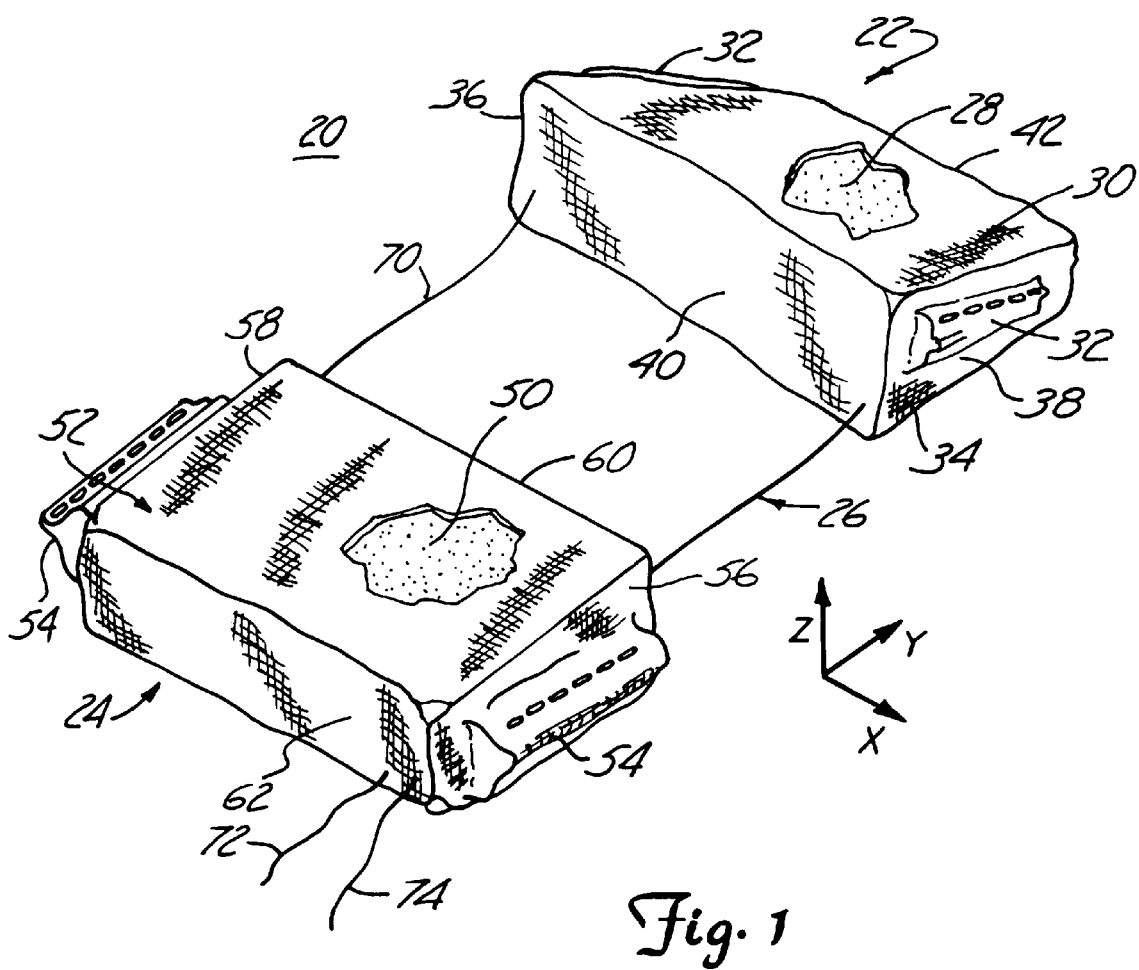
FIG. 1 is a perspective view of a prosthetic spinal disc nucleus, including cutaway views showing portions of hydrogel cores, in accordance with the present invention.

One preferred embodiment of a prosthetic spinal disc nucleus 20 is shown in FIG. 1. The prosthetic spinal disc nucleus 20 is comprised of a first prosthetic body 22, a second prosthetic body 24 and coupling means 26. As described in greater detail below, the coupling means 26 selectively associates the first prosthetic body 22 and the second prosthetic body 24.

The first prosthetic body 22 may assume a wide variety of different shapes and constructions. Preferably, however, for reasons made more clear below, the first prosthetic body 22 has a volume that is less than a volume of the nucleus cavity (not shown) into which the prosthetic spinal disc nucleus 20 will be implanted. Further, the first prosthetic body 22 is constructed to have sufficient structural integrity to maintain a desired separation between adjacent vertebrae (not shown) following implantation.

In one preferred embodiment, the first prosthetic body 22 is comprised of a hydrogel core 28 and a constraining jacket 30. The constraining jacket 30 is secured about the hydrogel core 28 by closures 32 located at opposite ends of the constraining jacket 30. With this construction, the hydrogel core 28 is configured to imbibe fluids, expanding from a dehydrated state to a hydrated state.

The preferred construction of the first prosthetic body 22, including the hydrogel core 28 and the constraining jacket 30, can assume a number of different shapes and sizes. Examples of acceptable constructions are provided in Ray et al., U.S. Pat. No. 5,824,093 and U.S. patent application Ser. No. 09/090,820, the teachings of which are incorporated herein by reference. In general terms, the hydrogel core 28 is preferably formulated as a mixture of hydrogel polyacrylonitrile. In particular, acrylamide and acrylonitrile (block co-polymer) are used. Alternatively, the hydrogel core 28 can be any hydrophilic acrylate derivative with a unique multi-block co-polymer structure or any other hydrogel material having the ability to deform and reform in a desired fashion in response to placement and removal of loads. Even further, a biologically safe polymer configured to maintain its structural integrity under various stresses is acceptable. For example, the hydrogel core 28 can be formulated as a mixture of polyvinyl alcohol and water. Much like a normal nucleus, the hydrogel core 28 will initially swell from a dehydrated state as it absorbs fluid. When hydrated, the hydrogel core 28 will have water content of 25–90 percent. The hydrogel material used for the hydrogel core 28 in the preferred embodiment is manufactured under the trade name HYPAN® by Hymedix International, Inc. of Dayton, N.J.

Again with reference to one preferred embodiment of the first prosthetic body 22, the constraining jacket 30 is preferably a flexible tube made of tightly woven high molecular weight, high tenacity polymeric fabric. For example, in one preferred embodiment, high molecular weight polyethylene is used as the weave material for the constraining jacket 30. However, polyester or any other high tenacity polymeric material can be employed, and carbon fiber yarns, ceramic fibers, metallic fibers, etc., are also acceptable.

The constraining jacket 30 is preferably made of fibers that have been highly orientated along their length. As a result, the constraining jacket 30 material, while flexible, has little elasticity or stretch. The constraining jacket 30 defines a generally fixed maximum volume, including a generally fixed length (x-axis of FIG. 1). In one preferred embodiment, the generally fixed maximum volume of the constraining jacket 30 is less than a theoretical volume of the hydrogel core 28 if allowed to completely hydrate without constraint. Thus, because the hydrogel core 28 has a natural, fully hydrated volume greater than the constraining jacket 30, the constraining jacket 30 will be tight about the hydrogel core 28 when hydrated, as described in greater detail below.

The preferred woven construction of the constraining jacket 30 creates a plurality of small openings 34 (shown generally in FIG. 1). Each of the plurality of small openings 34 is large enough to allow bodily fluids to interact with the hydrogel core 28 otherwise maintained within the constraining jacket 30. However, each of the plurality of small openings 34 is small to prevent the hydrogel core 28 from escaping. Each of the plurality of small openings 34 preferably has an average diameter of 10 micrometers, although other dimensions are acceptable. In this regard, although the constraining jacket 30 has been described as having a woven configuration, any other configuration having a semi-permeable or porous attribute can be used.

By employing a hydrogel core 28, the one preferred embodiment of the first prosthetic body 22 can be manufactured to assume different shapes in either the dehydrated or hydrated state. For example, the hydrogel core 28 may be fabricated to have an angled, tapered shape in the hydrated state as shown in FIG. 1. Alternatively, the hydrogel core 28 may be rectangular, wedged, circular, etc. in the hydrated state. In a dehydrated state, the hydrogel core 28 may have a shape corresponding to the hydrated state, or may have a different shape.

It should be understood that the first prosthetic body 22 can assume a wide variety of forms, and need not include the hydrogel core 28 or the constraining jacket 30 described above with reference to the preferred embodiment. Instead, the first prosthetic body 22 may be made of a natural or synthetic material, such as metal or plastic, or a combination of different materials. Further, the first prosthetic body 22 may be rigid or pliable and may include other features, such as ball bearings, springs, teeth, etc. The prosthetic body 22 need only have a volume that is less than a volume of the nucleus cavity (not shown) and sufficient structural integrity to maintain a desired spacing between adjacent vertebrae (not shown).

Regardless of exact construction, the first prosthetic body 22 generally defines a leading end 36 (partially shown in FIG. 1) and a trailing end 38. As described in greater detail below, the leading end 36 and the trailing end 38 are in reference to a preferred orientation of the first prosthetic body 22 during an implantation procedure. Further, the first prosthetic body 22 generally defines an interior face 40 and an opposing, exterior face 42 (partially shown in FIG. 1). As described in greater detail below, the interior face 40 and the exterior face 42 are in reference to a preferred orientation of the first prosthetic body 22 relative to the second prosthetic body 24 following implantation. For purposes of this disclosure, directional terminology such as "leading," "trailing," "interior" and "exterior" are with reference to one possible orientation of the first prosthetic body 22 during and following implantation. It should be understood, however, that the first prosthetic body 22 can be orientated in any direction relative to a nucleus cavity (not shown), the second prosthetic body 24 or the world in general. As such, the directional terms are provided for purposes of illustration only, and should not be interpreted as limitations.

The second prosthetic body 24 may or may not be similar to the first prosthetic body 22 in terms of size, shape and/or composition. In other words, much like the first prosthetic body 22, the second prosthetic body 24 may assume a wide variety of shapes and constructions, but preferably has a volume that is less than a volume of the nucleus cavity (not shown) and sufficient structural integrity to maintain a desired spacing between adjacent vertebrae (not shown).

In one preferred embodiment, the second prosthetic body 24 is comprised of a hydrogel core 50 and a constraining jacket 52. The constraining jacket 52 is secured about the hydrogel core 50 by closures 54 located at opposite ends of the constraining jacket 52. With this one preferred embodiment, the hydrogel core 50 and the constraining jacket 52 are virtually identical to that described above with reference to one preferred embodiment of the first prosthetic body 22. Once again, in general terms, the hydrogel core 50 can be fabricated to assume a wide variety of shapes of sizes. To this end, the hydrogel core 50 of the second prosthetic body 24 is shown in FIG. 1 as assuming a tapered configuration. Alternatively, the hydrogel core 50 may be manufactured to have the same shape as the hydrogel core 28 associated with the first prosthetic body 22. Along these same lines, the hydrogel core 50 of the second prosthetic body 24 may be larger, smaller or the same size as the hydrogel core 28 of the first prosthetic body 22.

As with the first prosthetic body 22, the second prosthetic body 24 is in no way limited to the preferred construction incorporating the hydrogel core 50 and the constraining jacket 52. Instead, different materials, or a combination of different materials, may be used. Additional features and/or components may also be incorporated. Thus, the second prosthetic body 24 may include metals, polymers, elastomers, etc. Notably, the second prosthetic body 24 may be made of an entirely different material or materials than the first prosthetic body 22. Regardless of exact construction, the second prosthetic body 24 generally defines a leading end 56, a trailing end 58 (shown partially in FIG. 1), an interior face 60 (shown partially in FIG. 1) and an exterior face 62. As described in greater detail below, the leading end 56 and the trailing end 58 are in reference to a preferred orientation of the second prosthetic body 24 during an implantation procedure. Further, the interior face 60 and the exterior face 62 are in reference to a preferred orientation of the second prosthetic body 24 relative to the first prosthetic body 22 following implantation.

The coupling means 26 selectively associates the first prosthetic body 22 with the second prosthetic body 24. More particularly, the coupling means 26 is preferably configured such that in a first position prior to implant, the second prosthetic body 24 can be displaced or otherwise maneuvered away from the first prosthetic body 22 a sufficient distance so that the first prosthetic body 22 can be implanted without interference from the second prosthetic body 24. Conversely, in a second, final assembly position following implantation, the coupling means 26 more closely associates the first and second prosthetic bodies 22, 24 such that the second prosthetic body 24 cannot be maneuvered or otherwise displaced from the first prosthetic body 22 by an appreciable distance. As a result, the first prosthetic body 22, via the coupling means 26, prevents undesired displacement of the second prosthetic body 24, and vice-versa. As described in greater detail below, the coupling means 26 is preferably related to the prosthetic bodies 22, 24 so as to facilitate rapid final assembly following implant. To this end, the coupling means 26 is configured so as to be connected to each of the prosthetic bodies immediately upon implant.

In one preferred embodiment, the coupling means 26 is a flexible, biocompatible thread or suture 70. Alternatively, for reasons made more clear below, the thread 70 material may be bioabsorbable, and may be radiopaque. Even further, the thread 70 may be inelastic, semi-elastic or elastic. Attachment of the thread 70 to the first and second prosthetic bodies 22, 24 is described in greater detail below. Generally speaking, however, the thread 70 includes a first end 72 and a second end 74. Further, at least a portion of the thread 70 is connected to the first prosthetic body 22 and another portion of the thread 70 is connected to the second prosthetic body 24 both prior to and following implant. As shown in the preferred embodiment of FIG. 1, a portion of the thread 70 connects the leading end 36 of the first prosthetic body 22 to the trailing end 58 of the second prosthetic body 24; and a separate portion of the thread 70 connects the trailing end 38 of the first prosthetic body 22 to the leading end 56 of the second prosthetic body 24. Alternatively, the thread 70 may be configured to connect only the trailing end 38 of the first prosthetic body 22 to the leading end 56 of the second prosthetic body 24.

While the coupling means 26 has been preferably described as being a thread 70, a number of alternative configurations may be employed. For example, the coupling means 26 may be a thin wire connecting the two prosthetic bodies 22, 24. Alternatively, the interior faces 40, 60 of the first and second prosthetic bodies 22, 24, respectively may include a releasable, mating bodies, for example a hook-and-loop connection material such as Velcro®. With this approach, the second prosthetic body 24 can easily be secured to and released from the first prosthetic body 22. A similar result may be achieved through use of opposing magnets disposed along the interior faces 40, 60. Alternatively, the coupling means 26 may be a flexible bag sized to maintain the first and second prosthetic bodies 22, 24, as described in greater detail below. Other examples of acceptable coupling means 26 include a biocompatible adhesive or glue coated along the interior faces 40, 60.

Regardless of exact construction, the coupling means 26 is preferably configured to allow movement of the second prosthetic body 24 relative to the first prosthetic body 22 in a first position, and in a second, final assembly position the second prosthetic body 24 is relatively fixed with respect to the first prosthetic body 22. For example, in one preferred embodiment in which the coupling means 26 is the thread 70, in a first position the second prosthetic body 24 is spaced from the first prosthetic body 22 as shown in FIG. 1. Because the thread 70 is flexible, the first and second prosthetic bodies 22, 24 are easily maneuvered independent of one another. However, in a second position (not shown), the extension of the thread 70 between the first and second prosthetic bodies 22, 24 is shortened and the first end 72 and the second end 74 secured. With this configuration, due to the limited extension of the thread 70 between the respective bodies 22, 24, the second prosthetic body 24 essentially cannot move independent of the first prosthetic body 22, and vice-versa.

Manufacture of a preferred embodiment of the prosthetic spinal disc nucleus 20 is substantially as follows. The first prosthetic body 22 and the second prosthetic body 24 are fabricated. For example, in the preferred embodiment, the hydrogel core 28 is secured within the constraining jacket 30 to form the first prosthetic body 22; and the hydrogel core 50 is secured within the constraining jacket 52 to form the second prosthetic body 24. Further details on the manufacture of the preferred embodiment of the first prosthetic body 22 and the second prosthetic body 24 are provided, for example in U.S. patent application Ser. No. 09/090,820, the teachings of which are incorporated herein by reference. Alternatively, where other constructions are used for the first prosthetic body 22 and/or the second prosthetic body 24, the necessary steps are taken to provide the first and second prosthetic bodies 22, 24 in a final form.

The coupling means 26 is then provided to selectively couple the first prosthetic body 22 to the second prosthetic body 24. In one preferred embodiment, and with reference to FIG. 2, the coupling means 26 is the thread 70 that is first passed through portions of the first and second prosthetic bodies 22, 24. It will be remembered that in the preferred embodiment, the first prosthetic body 22 includes the hydrogel core 28 and the constraining jacket 30; whereas the second prosthetic body 24 includes the hydrogel core 50 and the constraining jacket 52. Prior to implant, the respective hydrogel cores 28, 50 are preferably maintained in a dehydrated state such that a spacing exists between the hydrogel core 28, 50 and the respective constraining jacket 30, 52. With this in mind, the first end 72 of the thread 70 is first passed or woven through the constraining jacket 52 of the second prosthetic body 24 at the leading end 56, between the constraining jacket 52 and the hydrogel core 50. The first end 72 is then passed into the constraining jacket 30 of the first prosthetic body 22 at the trailing end 38. The first end 72 is threaded along the interior face 40 of the first prosthetic body 22, between the constraining jacket 30 and the hydrogel core 28. The thread 70 is then passed through the constraining jacket 30 at the leading end 36 and into the constraining jacket 52 of the second prosthetic body 24 at the trailing end 58. The first end 72 is then threaded along the interior face 60 of the second prosthetic body 24, between the hydrogel core 50 and the constraining jacket 52. Finally, the first end 72 is directed through the constraining jacket 52 of the second prosthetic body 24 at the leading end 56. In a final position, both the first end 72 and the second end 74 of the thread 70 extend from the exterior face 62 of the second prosthetic body 24.

Figure 2:
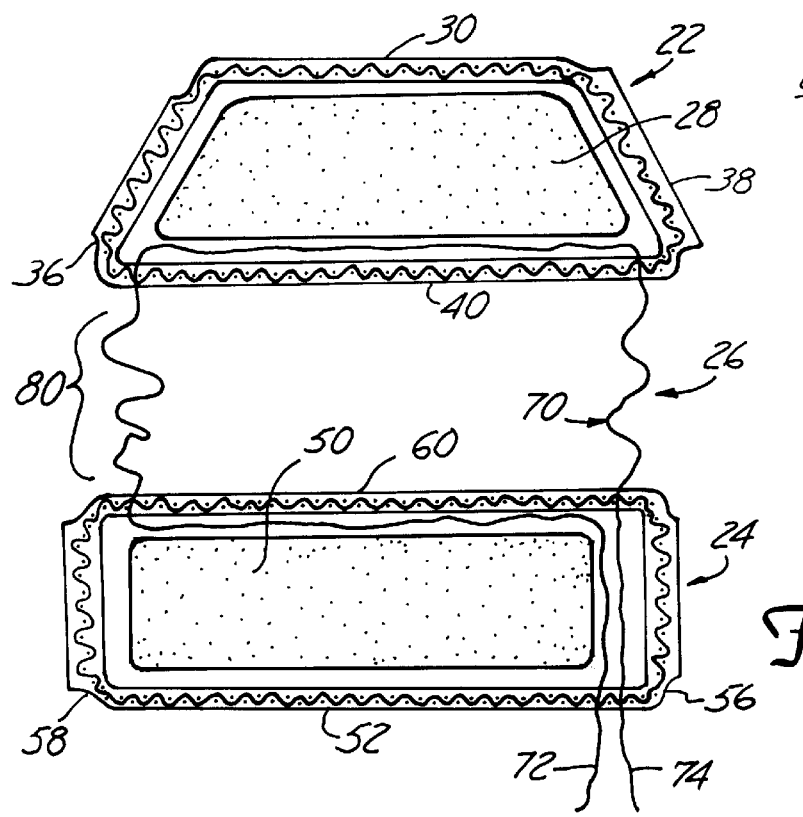
FIG. 2 is a top, sectional view of a prosthetic spinal disc nucleus in a dehydrated state in accordance with the present invention.
Figure 3:
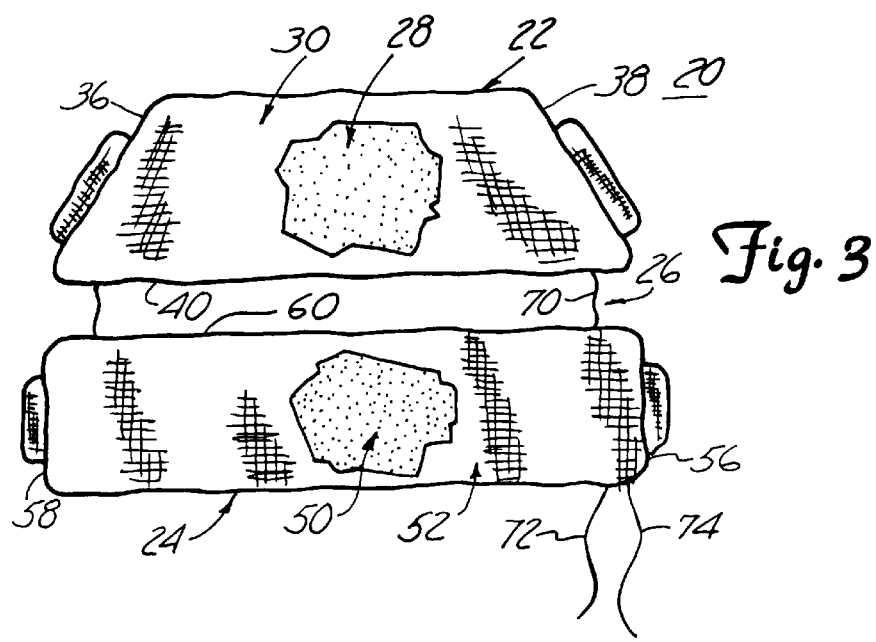
FIG. 3 is a top view of the prosthetic spinal disc nucleus in a hydrated state in accordance with the present invention.

As shown in FIG. 2, a slack 80 can be created where the thread 70 extends between the first and second prosthetic bodies 22, 24. With this approach, in a first position of the coupling means 26 (shown in FIG. 2), the slack 80 allows the second prosthetic body 24 to be moved away from the first prosthetic body 22 a certain distance when so desired. Further, in one preferred embodiment, the first prosthetic body 22 and the second prosthetic body 24 are slidable over the thread 70. For example, in the preferred embodiment, prior to implant, the respective hydrogel cores 28, 50, are in a dehydrated state such that the thread 70 is not "fixed" to the respective prosthetic body 22 or 24. Instead, the thread 70 is simply woven through the respective constraining jackets 30, 52. With this construction, the first prosthetic body 22 can be maneuvered away from the second prosthetic body 24, and vice-versa, by sliding the respective prosthetic body 22 or 24 along the thread 70. Conversely, the first end 72 and the second end 74 can be drawn away from the exterior face 62 of the second prosthetic body 24 to eliminate the slack 80 such that the first prosthetic body 22 and the second prosthetic body 24 are essentially fixed to one another in a second, final assembly position as shown in FIG. 3. As shown in FIG. 3, the slack 80 (FIG. 2) has been eliminated. In this second position, the first end 72 can be tied to the second end 74, thereby preventing movement of the second prosthetic body 24 independent of the first prosthetic body 22, and vice-versa. Additionally, in the preferred embodiment, where the respective hydrogel cores 28, 50 are allowed to hydrate and expand to a volumetric limit of the constraining jacket 30, 52, the prosthetic bodies 22, 24 themselves effectively limit sliding of the thread 70.

The above-described configuration of the coupling means 26 whereby the first and second prosthetic bodies 22, 24 are moveable relative to one another in a first position, and relatively fixed in a second, final assembly position can be accomplished with a number of different designs. For example, the coupling means 26 may be a thread secured at one end to the trailing end 38 of the first prosthetic body 22 and slidably secured to the leading end 56 of the second prosthetic body 24. With this relationship, the second prosthetic body 24 can be maneuvered along the thread away from or adjacent to the first prosthetic body 22. Alternatively, the coupling means 26 may be a set of magnets embedded within the first and second prosthetic bodies 22, 24. For example, a magnet may be positioned at the interior face 40 of the first prosthetic body 22. Similarly, a second magnet having an opposite polarity may be placed at the interior face 60 of the second prosthetic body 24. The magnetic strength associated with the magnets is selected such that a user can easily separate the first prosthetic body 22 from the second prosthetic body 24. However, when the second prosthetic body 24 is placed in close proximity to the first prosthetic body 22 (e.g., within five centimeters), the first and second prosthetic bodies 22, 24 are drawn to one another, via the magnets.

Figure 4:
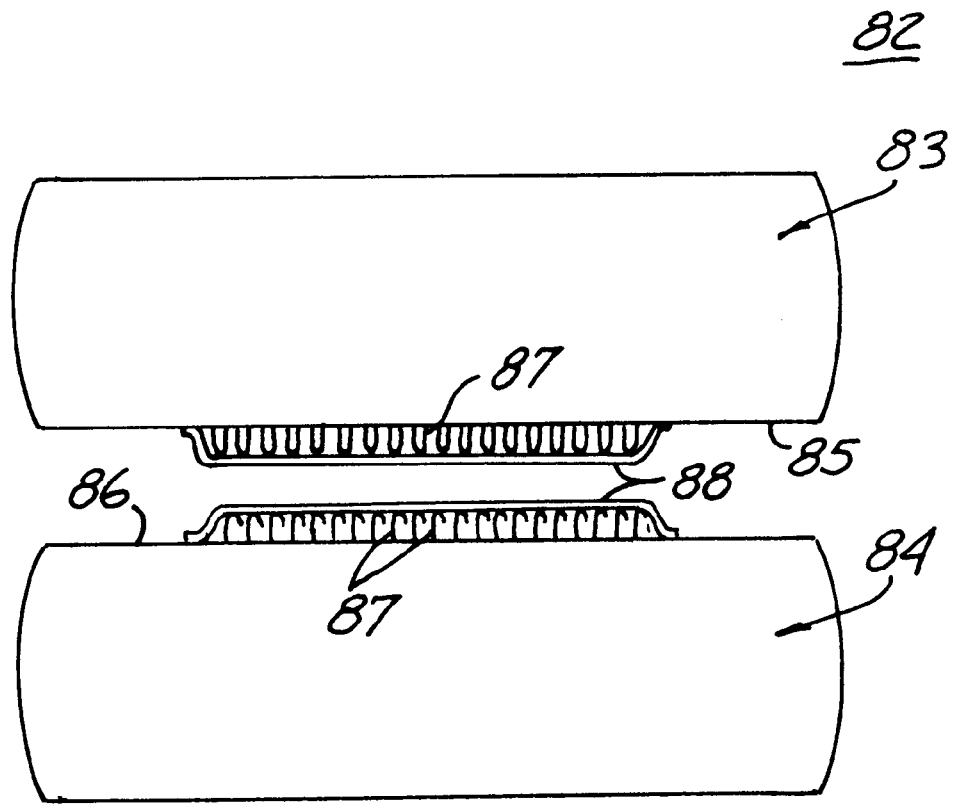
FIG. 4 is a top view of an alternative prosthetic spinal disc nucleus in accordance with the present invention.
Figure 5:
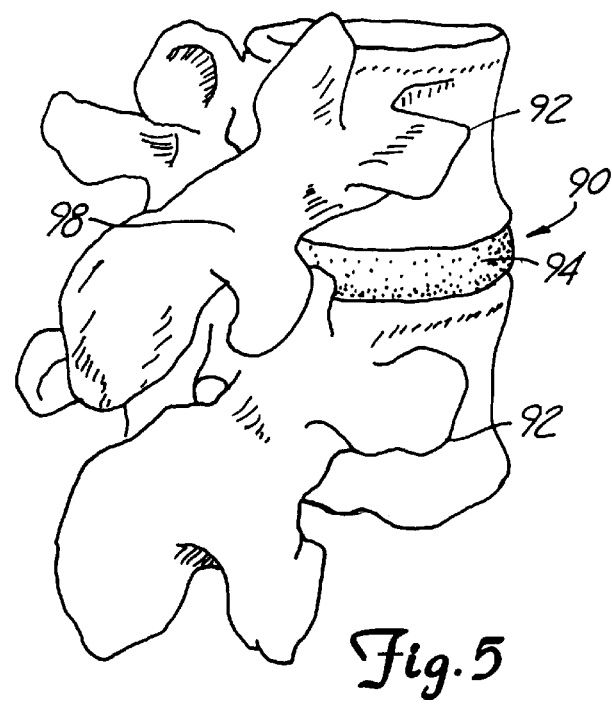
FIG. 5 is an elevated view of a spinal segment including a degenerated discal area.
Figure 6:
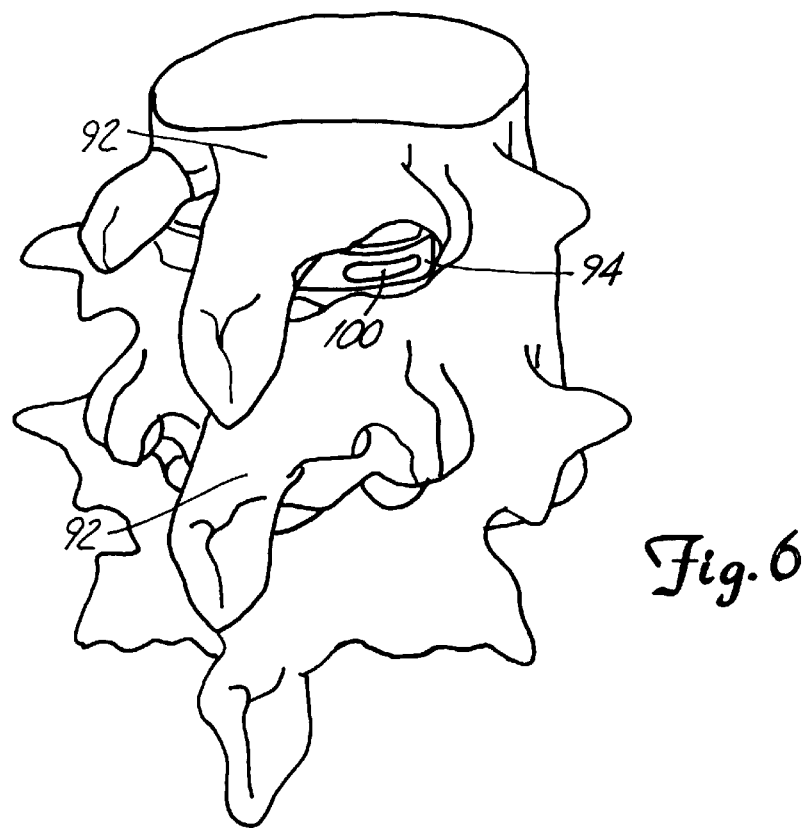
FIG. 6 is a posterior view of a portion of a human spine, showing an opening through an anulus.

A similar result can be achieved through use of mating bodies placed on the prosthetic bodies 22, 24, for example, a hook-and-loop material, such as Velcro®, may be employed. An alternative prosthetic spinal disc nucleus 82 incorporating a hook-and-loop design is shown in FIG. 4. The prosthetic spinal disc nucleus 82 includes a first prosthetic body 83 and a second prosthetic body 84. The first prosthetic body 83 includes an interior face 85. Similarly, the second prosthetic body 84 includes an interior face 86. A hook-and-loop material 87, such as Velcro®, is attached to a portion of each of the interior faces 83, 84. Finally, the hook-and-loop material 87 is coated with a bioabsorbable material 88. The bioabsorbable material 88 is preferably formulated to quickly dissolve when exposed to water or other body fluids. For example, in one preferred embodiment, the bioabsorbable material 88 is sorbitol. The hook-and-loop material 87 serves as a coupling means for selectively associating the first prosthetic body 83 with the second prosthetic body 84. For example, prior to implant, the first and second prosthetic bodies 83, 84 are not engaged to one another such that the second prosthetic body 84 does not impede implantation of the first prosthetic body 83. Further, because the hook-and-loop material 87 is coated with the bioabsorbable material 88, the hook-and-loop material 87 associated with the first prosthetic body 83 does not hinder desired placement of the second prosthetic body 84. However, shortly after implant, the bioabsorbable material 88 will dissolve, thereby allowing the second prosthetic body 84 to couple to the first prosthetic body 83 via the hook-and-loop material 87. Similar results may be achieved by positioning a male connector along the interior face 83, and a female connector along the interior face 84. Following implant, the first prosthetic body 83 can be directed toward the second prosthetic body such that the male connector engages the female connector.

Regardless of the exact configuration, the coupling means 26 preferably allows movement of the second prosthetic body 24 relative to the first prosthetic body 22 in a first position, and relatively rigidly connects the first and second prosthetic bodies 22, 24 in a second, final assembly position.

As previously described, the exact form of the first and second prosthetic bodies 22, 24 may vary greatly from the preferred embodiment shown in FIGS. 1–3. Regardless of the exact shape or construction, however, the preferred method of implantation is identical. For example, FIGS. 5–10 depict implantation of the prosthetic spinal disc nucleus 20 (FIGS. 1–3) into a damaged disc space 90. The disc space 90 separates adjacent vertebrae 92 and includes an anulus 94 and a nucleus region or cavity 96 (shown best in FIG. 7). Proper positioning is achieved by first performing a laminectomy in a targeted lamina area 98. A passage 100 is created through a posterior side of the anulus 94, either by simple incision or removal of a radial plug. If necessary, excess material is removed from the nucleus cavity 96 to create room for the prosthetic spinal disc nucleus 20. Although in this example, a single passage 100 is illustrated and discussed, a pair of passages may alternatively be used. Further, while a generally posterior technique has been identified, insertion through any portion of the anulus 94 is acceptable.

Figure 7:
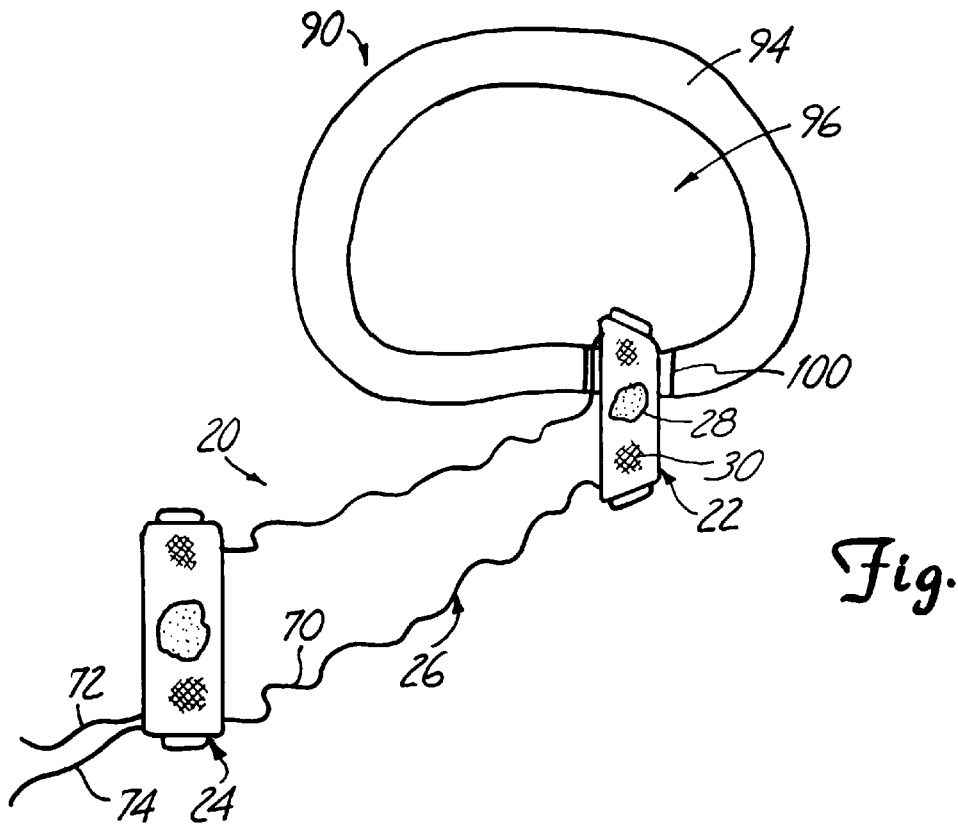
FIG. 7–10 illustrate implantation of a prosthetic spinal disc nucleus in accordance with the present invention into a discal segment.

The prosthetic spinal disc nucleus 20 is then implanted into the nucleus cavity 96 via the passage 100. Implantation of the prosthetic spinal disc nucleus 20 includes successive implantation of the first prosthetic body 22 and the second prosthetic body 24, beginning with insertion of the first prosthetic body 22 as shown in FIG. 7. Prior to insertion of the first prosthetic body 22, the second prosthetic body 24 is maneuvered away from the first prosthetic body 22 so as to not otherwise impede insertion of the first prosthetic body 22 through the passage 100. In this regard, the coupling means 26 allows for this desired movement. For example, where the coupling means 26 is the thread 70, the second prosthetic body 24 is moved along the thread 70 in a sliding fashion a sufficient distance away from the first prosthetic body 22 to allow for unimpeded insertion. Preferably, the second prosthetic body 24 is at least 10 centimeters away from the first prosthetic body 22. More preferably, the second prosthetic body 24 is a relatively large distance away from the first prosthetic body 22 such that the second prosthetic body 24 is maintained outside of the patient during the implantation procedure.

Figure 8:
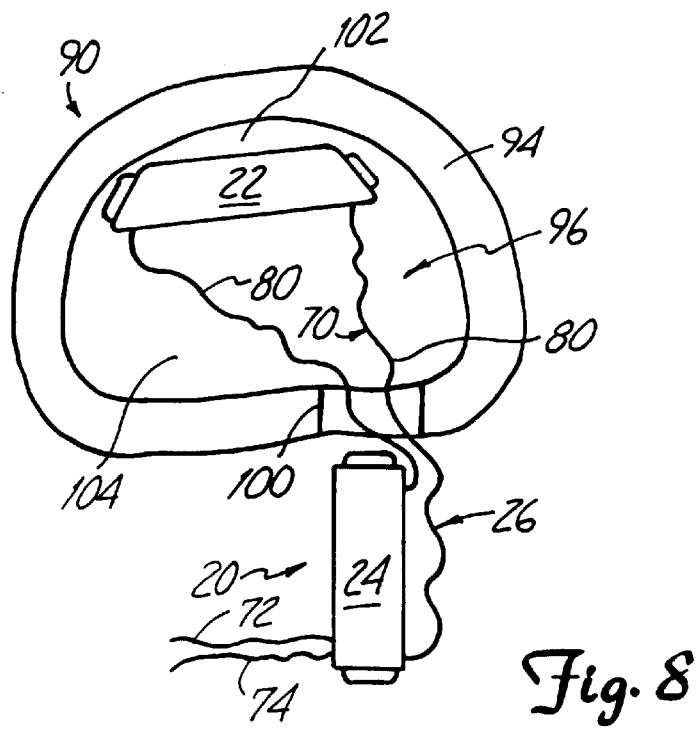

As previously described, in one preferred embodiment, the first prosthetic body 22 is comprised of the hydrogel core 28 and a constraining jacket 30. With this preferred construction, the hydrogel core 28 is dehydrated prior to insertion through the passage 100. In this dehydrated state, the first prosthetic body 22 is relatively small so as to easily slide through the passage 100. Once the first prosthetic body 22 is fully disposed within the nucleus cavity 96, the first prosthetic body 22 is preferably rotated to extend transversely within the nucleus cavity 96 as shown in FIG. 8. With reference to the orientation of FIG. 8, the disc space 90 can be generally defined by an anterior area 102 and a posterior area 104. With this in mind, the first prosthetic body 22 is positioned within the nucleus cavity 96 at the anterior area 102. If necessary, a rod and mallet (not shown) may be used to lodge the first prosthetic body 22 into the position shown in FIG. 8.

Figure 9:
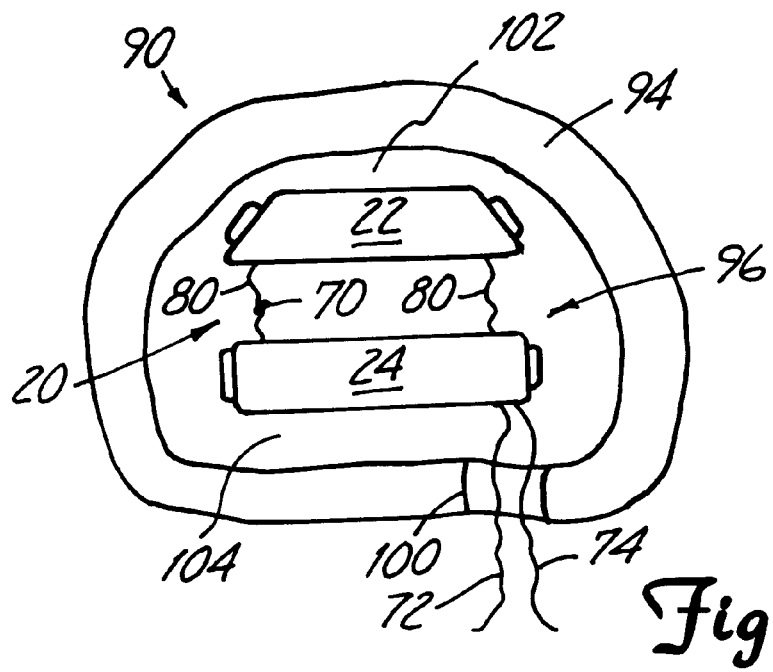

The second prosthetic body 24 is then similarly implanted through the passage 100 in the anulus 94. In a preferred embodiment, as the second prosthetic body 24 is maneuvered near the anulus 94, the slack 80 in the thread 70 is lessened by pulling on the first end 72 and the second end 74 of the thread 70. With the one preferred embodiment of the prosthetic spinal disc nucleus 20, the thread 70 is slidably connected to the second prosthetic body 24 prior to insertion. Thus, immediately following implant, the coupling means 26 is connected to the second prosthetic body 24. Once inserted, the second prosthetic body 24 is preferably rotated to extend transversely within the nucleus cavity 96, positioned at the posterior area 104 as shown in FIG. 9.

Figure 10:
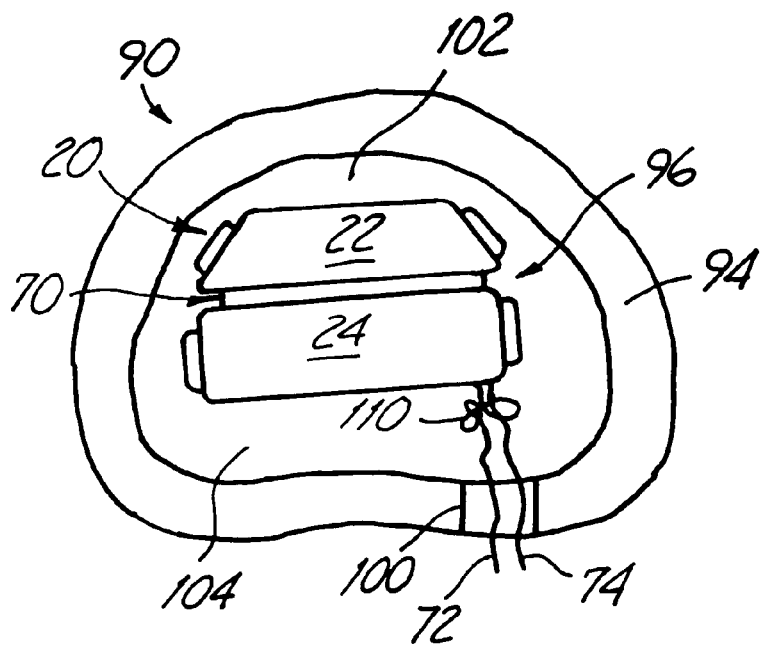
Figure 11:
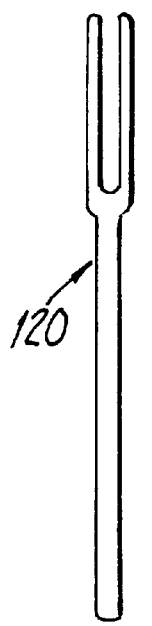
FIG. 11 is a top view of a tool used during implantation of a prosthetic spinal disc nucleus in accordance with the present invention.

With both the first prosthetic body 22 and the second prosthetic body 24 placed within the nucleus cavity 96, the first end 72 and the second end 74 of the thread 70 are retracted so as to draw the second prosthetic body 24 into close proximity with the first prosthetic body 22. Because the thread 70 is already connected to both of the prosthetic bodies 22, 24, the surgeon is not faced with the task of somehow connecting the thread to prosthetic bodies 22, 24 within the small confines of the nucleus cavity 96. Retraction of the thread 70 removes virtually all of the slack 80 in the thread 70 so that the second prosthetic body 24 is effectively fixed to the first prosthetic body 22 in a final assembly position. As shown in FIG. 10, a knot 110 is formed in the thread 70 by tying the first end 72 to the second end 74. Formation of the knot 110 can be facilitated, for example, by use of two-pronged tool 120 shown in FIG. 11. The tool 120 assists in pushing the knot 110 as close as possible to the second prosthetic body 24.

Figure 12:
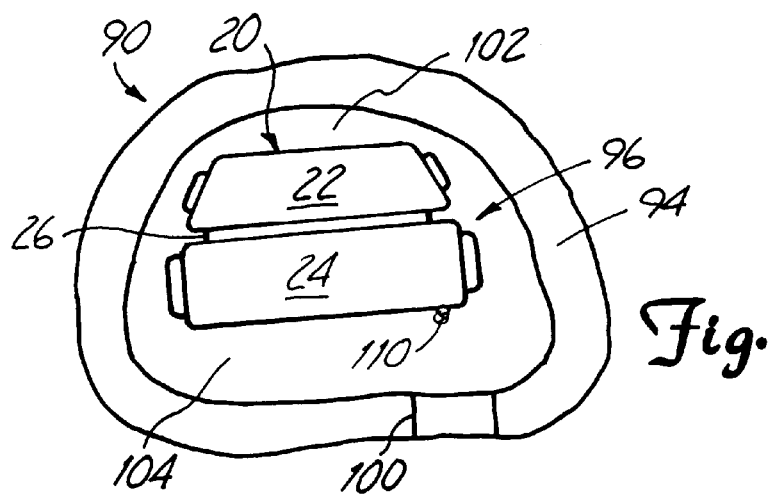
FIG. 12 is a top, sectional view of a disc space having a prosthetic spinal disc nucleus implanted and in a dehydrated state.

After formation of the knot 110, any excess thread material is removed proximal the knot 110 as shown in FIG. 12.

By coupling the first prosthetic body 22 and the second body 24, the coupling means 26 essentially prevents undesired movement of the prosthetic spinal disc nucleus 20 back through the passage 100 in the anulus 94. In other words, while the first prosthetic body 22 and the second prosthetic body 24 may, individually, be small enough to slip back through the passage 100, once joined together, the collective prosthetic spinal disc nucleus 20 is much larger than the passage 100. Further, as previously described, the first prosthetic body 22 is preferably lodged within the nucleus cavity 96. By coupling the second prosthetic body 24 to the first prosthetic body 22, then, the first prosthetic body 22 serves as an anchor so that the second prosthetic body 24 will not accidentally rotate and move backward through the passage 100. Further, where the coupling means 26 includes a radiopaque characteristic, the coupling means 26 will provide a visual indication of positioning of the prosthesis 20.

Figure 13:
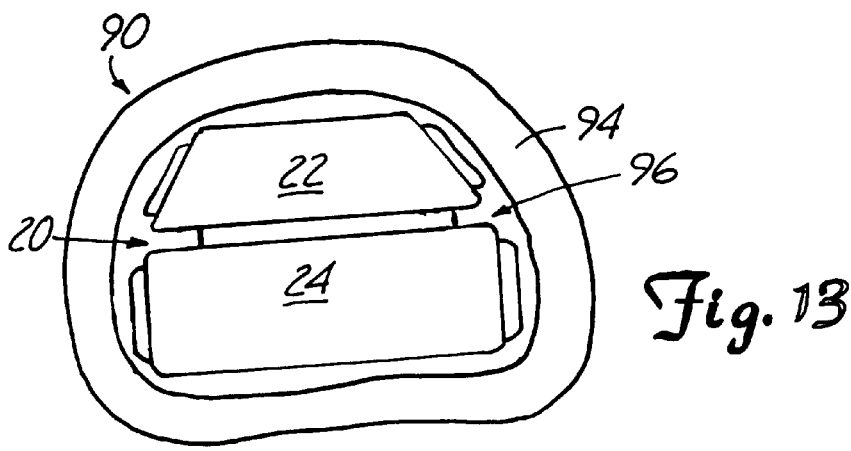
FIG. 13 is a top, sectional view of a disc space having a prosthetic spinal disc nucleus implanted and in a hydrated state.

Finally, with a preferred construction of the first prosthetic body 22 and the second prosthetic body 24 including the hydrogel cores 28, 50 and the constraining jackets 30, 52, respectively, following implantation, the hydrogel cores 28, 50 are allowed to hydrate. Following hydration, the prosthetic spinal disc nucleus 20 encompasses a majority of the nucleus cavity 96 as shown in FIG. 13. Further, in one preferred embodiment, the thread 70 is comprised of bioabsorbable material that will dissolve over time. With this configuration, the coupling of the first and second prosthetic bodies 22, 24 will no longer exist after a certain period, for example, one-month. However, this one month period is likely sufficient for the first and second prosthetic bodies 22, 24 to hydrate to a level whereby they will not unexpectedly move back through the passage 100.

In the position of FIG. 13, the prosthetic spinal disc nucleus 20 functions as an intervertebral spacer and a cushion. Depending upon the exact construction of the first prosthetic body 22 and the second prosthetic body 24, the prosthetic spinal disc nucleus 20 may also potentially restore the normal fluid pumping action of the disc space 90. It should be understood that actual performance of the prosthetic spinal disc nucleus 20 will depend upon the composition of the first and second prosthetic bodies 22, 24. In this regard, where the first and second prosthetic bodies 22, 24 employ the hydrogel cores 28, 50 (FIG. 1), the prosthetic spinal disc nucleus 20 will expand to separate the adjacent vertebrae 92. Functioning of this preferred embodiment of the prosthetic spinal disc nucleus 20 is described in greater detail in U.S. patent application Ser. No. 09/090,820, the teachings of which are incorporated herein by reference. As previously described, a wide variety of other constructions and materials can be used for the first and second prosthetic bodies 22, 24. The prosthetic spinal disc nucleus 20 will perform in accordance with the design characteristics associated with each individual construction.

As indicated above, the coupling means 26 can vary greatly from the thread 70 shown in the preferred embodiment, yet still allow unimpeded insertion of the first prosthetic body 22 in a first position prior to implant and limit movement of the second prosthetic body 24 relative to the first prosthetic body 24 in a second, final assembly position following implant. For example, the coupling means 26 can be mating bodies positioned along the prosthetic bodies (such as hook-and-loop material previously described). With this technique, at least a portion of the coupling means 26 is connected to each of the prosthetic bodies prior to implant, and thus immediately after implant. As a result, the only minimal efforts are required by the surgeon to achieve a final assembly or coupling between the prosthetic bodies.

Figure 14:
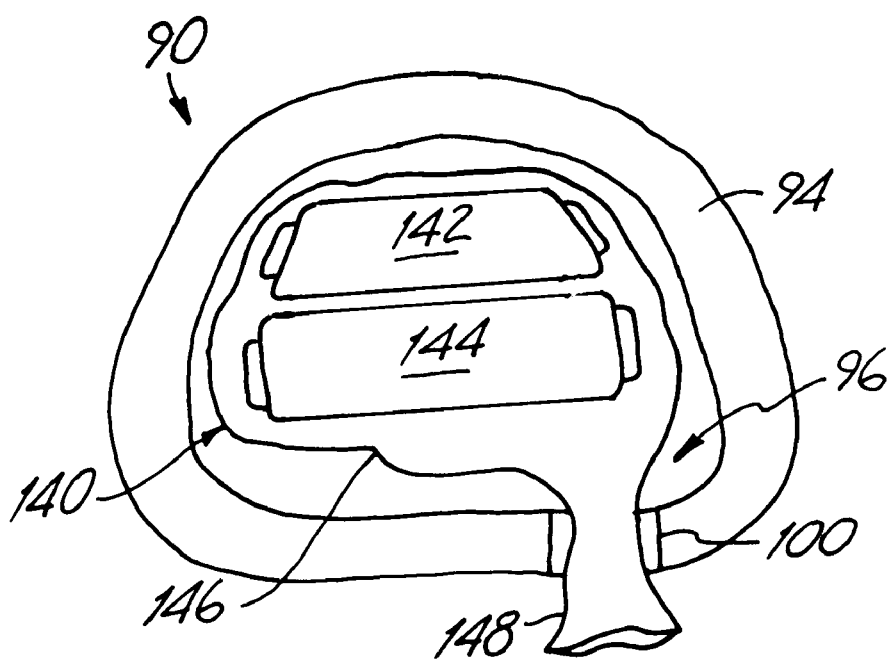
FIG. 14 is a top, sectional view of a disc space having an alternative prosthetic spinal disc nucleus implanted.

FIG. 14 depicts yet another alternative embodiment of a prosthetic spinal disc nucleus 140 implanted in the nucleus cavity 96. The prosthetic spinal disc nucleus 140 includes a first prosthetic body 142, a second prosthetic body 144 and a coupling means in the form of a flexible bag 146. The flexible bag 146 is preferably made of a biocompatible material that is inelastic, semi-elastic or elastic, and is sized to maintain the first and second prosthetic bodies 142, 144. To this end, the flexible bag 146 is preferably porous and has a volume slightly larger than a combined volume of the first prosthetic body 142 and the second prosthetic body 144. Finally, the flexible bag 146 forms an open end 148.

During use, the flexible bag 146 is inserted into the nucleus cavity 96 via the passage 100. The open end 148 is aligned with the passage 100. The first and second prosthetic bodies 142, 144 are then successively implanted and preferably rotated to a desired position. In this regard, the prosthetic bodies 142, 144 are implanted into the flexible bag 146 through the open end 148. Notably, immediately after insertion, each of the prosthetic bodies 142, 144 are encompassed by, and therefore in contact with, the flexible bag 146. The open end 148 is then sewn shut and any excess material is forced through the passage 100 into the nucleus cavity 96. The flexible bag 146 allows the first prosthetic body 142 to be implanted without interference from the second prosthetic body 144. By closing the open end 148, the second prosthetic body 144 cannot escape from the flexible bag 146. The flexible bag 146 effectively couples the first prosthetic body 142 with the second prosthetic body 144, the combination being much larger in size than the passage 100. Thus, first prosthetic body 142 and the second prosthetic body 144 cannot independently move back through the passage 100. Additionally, once implanted, the flexible body 146 limits movement of the second prosthetic body 144 relative to the first prosthetic body 142 such that the second prosthetic body 144 will not experience undesired displacement back through the passage 100.

The prosthetic spinal disc nucleus of the present invention: (a) restores or maintains the height of a damaged disc space; (b) restores and tightens the natural anulus to stop further degeneration and permit its healing; (c) allows the use of a minimally invasive surgical procedure that provides both cost and medical benefits; and (d) provides a device that is implantable with minimal damage to the anulus, yet able to resist undesired expulsion of any portion of the prosthetic spinal disc nucleus outwardly from the nucleus cavity. In particular, a prosthetic spinal disc nucleus having an overall volume approaching a volume of the nucleus cavity is divided into smaller, individual bodies. Due to their reduced size, these individual bodies require only a small opening in the anulus to be implanted. Once fully inserted, however, the coupling means facilitates an effective "connection" of the individual bodies into a final device that is not susceptible to unexpected extrusion back through the opening in the anulus.

Although the present invention has been described with reference to preferred embodiments, workers skilled in the art will recognize that changes may be made in form and detail without departing from the spirit and scope of the invention. For example, in the preferred embodiment, the prosthetic spinal disc nucleus has been shown as having two prosthetic bodies. It should be recognized that a prosthetic spinal disc nucleus in accordance with the present invention may have three or more individual bodies selectively associated by a coupling means. Each individual prosthetic body may be identical to one another, or may be of a different shape, size, construction, etc. Once again, however, the coupling means allows each individual body to be inserted without interference from the others through a relatively small opening in the anulus, yet effectively "fixes" or otherwise associates each body to another following implant. Similarly, in a preferred embodiment, the prosthetic bodies have been shown as being orientated to extend transversely within the nucleus cavity. This orientation is in no way required. Instead, the prosthetic bodies can be positioned anywhere within the nucleus cavity. For example, the prosthetic bodies may be orientated to extend sagitally within the nucleus cavity.

What is claimed is:

1. A prosthetic spinal disc nucleus for implantation into a nucleus cavity defined by an opposing pair of vertebrae and an anulus, the prosthetic spinal disc nucleus comprising:
   a first prosthetic body having sufficient structural integrity for separating an opposing pair of vertebrae and a volume that is less than a volume of a nucleus cavity;
   a second prosthetic body having sufficient structural integrity for separating an opposing pair of vertebrae and a volume that is less than a volume of a nucleus cavity;
   coupling means for selectively associating the first prosthetic body with the second prosthetic body, the coupling means configured to allow successive implantation of the first prosthetic body and then the second prosthetic body through an opening in the anulus and to substantially affix the first prosthetic body to the second prosthetic body upon implantation and final assembly; and
   wherein immediately following implantation of the second prosthetic body, the coupling means is connected to each of the first and second prosthetic bodies for relatively rapidly achieving the final assembly.

2. The prosthetic spinal disc nucleus of claim 1, wherein the first and second prosthetic bodies each have a volume that is less than one-half of a volume of the nucleus cavity.

3. The prosthetic spinal disc nucleus of claim 1, wherein the first and second prosthetic bodies each include a hydrogel core encompassed by a constraining jacket having a generally fixed maximum volume that is less than a volume of the nucleus cavity.

4. The prosthetic spinal disc nucleus of claim 1, wherein the coupling means is a biocompatible thread.

5. The prosthetic spinal disc nucleus of claim 4, wherein the thread is slidably connected to at least one of the first and second prosthetic bodies such that in an initial position prior to implantation, an extension of the thread between the first and second prosthetic bodies is variable, whereas in the final assembly position following implantation, the extension is relatively fixed.

6. The prosthetic spinal disc nucleus of claim 4, wherein each of the first and second prosthetic bodies includes a core material surrounded by a jacket, and further wherein a first portion of the thread is connected to the jacket of the first prosthetic body and a second portion of the thread is connected to the jacket of the second body.

7. The prosthetic spinal disc nucleus of claim 4, wherein the thread is comprised of a bioabsorbable material.

8. The prosthetic spinal disc nucleus of claim 1, wherein the first and second prosthetic nucleus bodies each define a leading end and a trailing end, and further wherein the coupling means is configured to connect the trailing end of the first prosthetic body to the leading end of the second prosthetic body.

9. The prosthetic spinal disc nucleus of claim 8, wherein the coupling means is further configured to connect the leading end of the first prosthetic body to the trailing end of the second prosthetic body.

10. The prosthetic spinal disc nucleus of claim 1, wherein the nucleus cavity is definable by an anterior area and a posterior area, the first prosthetic body being configured for placement in the anterior area, and further wherein the coupling means is configured to prevent displacement of the second prosthetic body from the posterior area.

11. The prosthetic spinal disc nucleus of claim 1, wherein the coupling means is a flexible bag sized to receive both the first prosthetic body and the second prosthetic body.

12. The prosthetic spinal disc nucleus of claim 1, wherein upon final implantation, the first prosthetic body defines an interior face proximate an interior face of the second prosthetic body, and further wherein the coupling means includes corresponding mating bodies positioned at each of the interior faces, respectively, for securing the first prosthetic body to the second prosthetic body.

13. The prosthetic spinal disc nucleus of claim 12, wherein the mating bodies are hook-and-loop material.

14. A method of manufacturing a prosthetic spinal disc nucleus for implantation into a nucleus cavity defined by an opposing pair of vertebrae and an anulus, the method including:

forming a first prosthetic body having sufficient structural integrity for separating an opposing pair of vertebrae and a volume that is less than a volume of a nucleus cavity;

forming a second prosthetic body having sufficient structural integrity for separating an opposing pair of vertebrae and a volume that is less than a volume of a nucleus cavity; and providing a coupling device to selectively couple the first prosthetic body to the second prosthetic body such that a distance between the first and second prosthetic bodies is variable in a first state, and relatively fixed in a second state, at least a portion of the coupling device being connected to both the first and second prosthetic bodies immediately following implantation.

15. The method of claim 14, wherein forming a first prosthetic body includes securing a hydrogel core within a constraining jacket and forming a second prosthetic body includes securing a hydrogel core within a constraining jacket, each of the constraining jackets having a generally fixed maximum volume that is less than one-half a volume of a nucleus cavity.

16. The method of claim 14, wherein the coupling device is a flexible thread, the method further including:

connecting the first prosthetic body to the second prosthetic body with the flexible thread.

17. The method of claim 16, wherein each of the first and second prosthetic bodies includes a jacket comprised of a woven material, and further wherein connecting the first prosthetic body to the second prosthetic body includes:

weaving a first portion of the flexible thread into the constraining jacket of the first prosthetic body; and weaving a second portion of the flexible thread into the constraining jacket of the second prosthetic body.

18. The method of claim 16, wherein connecting the first prosthetic body to the second prosthetic body includes:

slidably securing a first portion of the flexible thread to the first prosthetic body; and slidably securing a second portion of the flexible thread to the second prosthetic body.

19. The method of claim 16, wherein during an implantation procedure, the first and second prosthetic bodies each define a leading end and a trailing end, and wherein connecting the first prosthetic body to the second prosthetic body includes:

directing the thread from the leading end of the second prosthetic body to the trailing end of the first prosthetic body;

extending the thread from the trailing end of the first prosthetic body to the leading end of the first prosthetic body; and directing the thread from the leading end of the first prosthetic body to the trailing end of the second prosthetic body.

20. The method of claim 14, wherein the coupling device is a flexible bag, the method further including:

placing the first and second prosthetic bodies within the flexible bag following locating of the flexible bag in a nucleus cavity.

21. A method of implanting a prosthetic spinal disc nucleus into a nucleus cavity defined by an opposing pair of vertebrae and an anulus, the prosthetic spinal disc nucleus including a first prosthetic body and a second prosthetic body, each of the prosthetic bodies having sufficient structural integrity to separate the opposing pair of vertebrae and a volume that is less than a volume of the nucleus cavity, the method including:

providing a coupling device to selectively couple the first prosthetic body to the second prosthetic body;

forming an opening in the anulus;

inserting the first prosthetic body into the nucleus cavity through the opening in the anulus, the coupling device being configured such that the second prosthetic body does not impede insertion of the first prosthetic body and at least a portion of the coupling device being connected to the first prosthetic body immediately after insertion;

lodging the first prosthetic body in the nucleus cavity;

inserting the second prosthetic body into the nucleus cavity such that at least a portion of the coupling device is connected to the second prosthetic body immediately after insertion; and positioning the coupling device such that the first prosthetic body prevents displacement of the second prosthetic body back through the opening in the anulus.

22. The method of claim 21, wherein the coupling device is a flexible thread, the method further including:

connecting the first prosthetic body to the second prosthetic body with the flexible thread before inserting the first prosthetic body.

23. The method of claim 22, wherein the flexible thread is slidably connected to the first prosthetic body and to the second prosthetic body, the method further including:

sliding the second prosthetic body away from the first prosthetic body prior to inserting the first prosthetic body.

24. The method of claim 23, further including:

securing the flexible thread after inserting the second prosthetic body to limit movement of the second prosthetic body relative to the first prosthetic body.

25. The method of claim 21, wherein the coupling device is a flexible bag sized to receive the first and second prosthetic bodies and having an open end, the method further including:

inserting the flexible bag into the nucleus cavity such that the open end is aligned with the opening in the anulus, wherein the first and second prosthetic bodies are inserted into the flexible bag through the open end; and closing the open end.

26. The method of claim 21, wherein the coupling device includes a first portion positioned along the first prosthetic body and a second portion positioned along the second prosthetic body, and further wherein positioning the coupling device includes:

directing the second prosthetic body toward the first prosthetic body such that the second portion engages the first portion.

27. The method of claim 21, wherein the first and second prosthetic bodies each include a hydrogel core encompassed by a constraining jacket, the method further including:

dehydrating the first and second prosthetic bodies prior to insertion into the nucleus cavity.

* * * * *